United States Patent [19]
Wayne et al.

[11] Patent Number: 5,137,021
[45] Date of Patent: Aug. 11, 1992

[54] LEAD CURRENT MEASUREMENT CIRCUIT

[75] Inventors: David A. Wayne, Scottsdale; Tho Huynh, Mesa, both of Ariz.

[73] Assignee: Medtronic, Inc., Minneapolis, Minn.

[21] Appl. No.: 619,494

[22] Filed: Nov. 29, 1990

[51] Int. Cl.$^5$ .............................................. A61N 1/08
[52] U.S. Cl. .............................................. 128/419 PT
[58] Field of Search ............. 128/419 PG, 419 PT, 128/419 D

[56] References Cited

U.S. PATENT DOCUMENTS

| | | | |
|---|---|---|---|
| 3,747,605 | 7/1973 | Cook | 128/419 D |
| 3,886,950 | 6/1975 | Ukkestad et al. | 128/419 D |
| 4,087,637 | 5/1978 | DeKont | 128/419 PT |
| 4,141,367 | 2/1979 | Ferreira | 128/419 PT |
| 4,332,256 | 6/1982 | Brownlee et al. | 128/419 PT |
| 4,337,776 | 7/1982 | Daly et al. | 128/419 PT |
| 4,364,396 | 12/1982 | Barthel | 128/419 PT |
| 4,606,350 | 8/1986 | Frost | 128/419 PG |
| 4,899,750 | 2/1990 | Ekwall | 128/419 PG |
| 4,949,720 | 8/1990 | Thompson | 128/419 PG |

FOREIGN PATENT DOCUMENTS 0338363 10/1989 European Pat. Off. .

OTHER PUBLICATIONS

"Atrial Pacing: Efficacy and Safety", Pace, vol. 12, Jul. 1989, Part 1, pp. 1049-1054.

*Primary Examiner*—William E. Kamm
*Assistant Examiner*—Kennedy J. Schaetzle
*Attorney, Agent, or Firm*—Harold R. Patton; John A. Rissman; John L. Rooney

[57] ABSTRACT

An apparatus for and method of measuring the current which flows through a cardiac pacing lead to artificially stimulate contractions of the myocardium. This current measurement is useful for estimating battery life and monitoring proper operation of the pacing lead and the implantable pulse generator.

The measurement is accomplished by carefully controlling the gain of the output amplifier and timing the rate of charge and discharge of the output capacitor. The average pacing current can be determined from the relative charge and discharge times given that the other circuit component values are known and controlled.

9 Claims, 5 Drawing Sheets

LEAD CURRENT MEASUREMENT CIRCUIT

BACKGROUND OF THE INVENTION

1. Field of the Invention

The present invention generally relates to implantable medical devices, and more particularly, relates to implantable cardiac pacing devices.

2. Description of the Prior Art

The medical treatment of bradycardia by artificial cardiac pacing has been known for some time. Currently, such treatment using an implantable pulse generator electrically coupled to the myocardial tissue via an insulated lead is well accepted.

Much has been done concerning efficiency of the therapy in relation to the acute and chronic condition of the pacing lead and electrode positioning. "Atrial Pacing: Efficacy and Safety" by Kerr, et al., Pace, Volume 12, July 1989, pages 1049-1054, describes a study of atrially paced patients. It is apparent from such studies that the ability to measure various lead parameters both acutely and chronically is most desirable.

Acute measurement of certain lead parameters can be accomplished using a pacing system analyzer. Typically this is an external device which is used at the time of implant to verify proper lead position and function. U.S. Pat. No. 4,141,367 issued to Ferreira describes such a pacing system analyzer which measures lead impedance as computed by measuring output capacitor voltage before and after delivery of a pacing pulse. U.S. Pat. No. 4,364,396 issued to Barthel teaches a pacing system analyzer which measures output energy by sensing output capacitor voltage before and after pacing.

Lead impedance and pulse output measurements are also made chronically by some implantable pulse generators. Normally this data is subsequently telemetered external to the patient for display and analysis. U.S. Pat. No. 4,332,256 issued to Brownlee et al., discusses an implantable pulse generator which uses change in voltage across the output capacitor to determine lead impedance. U.S. Pat. No. 4,899,750 issued to Ekwall uses a similar technique to prepare a moving average of the lead impedance value. European Patent Application No. 0 338 363 in the name of Hafelfinger et al., suggests that lead impedance measurements should be made automatically upon the occurrence of various events.

U.S. Pat. No. 4,337,776 issued to Daly et al., proposes to measure lead impedance by monitoring successive output pulses of different amplitude. U.S. Pat. No. 4,949,720 issued to Thompson measures lead current directly by monitoring the current through FET devices in parallel with the main output path.

SUMMARY OF THE INVENTION

The present invention overcomes the disadvantages of the prior art by providing a technique to measure pacing lead current indirectly without requiring precision measurement of the output pulse voltage. To accomplish this, the present invention uses an amplifier and switched capacitors to set a reference threshold accurately related to the voltage lost from the capacitor during an output pulse. Using this threshold, the lead current can be easily determined by measuring the output pulse width and the length of time required to discharge the capacitor to the threshold determined by the output amplifier.

Computing lead current by measuring output capacitor discharge time, rather than monitoring voltage drop across the output capacitor or sensing current flow in the lead circuit directly, promotes greater accuracy. In addition, this technique does not require accurate knowledge of the output capacitor value. Furthermore, because of the simplicity of the components, the circuitry is suitable for implementation in either external or implantable form.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
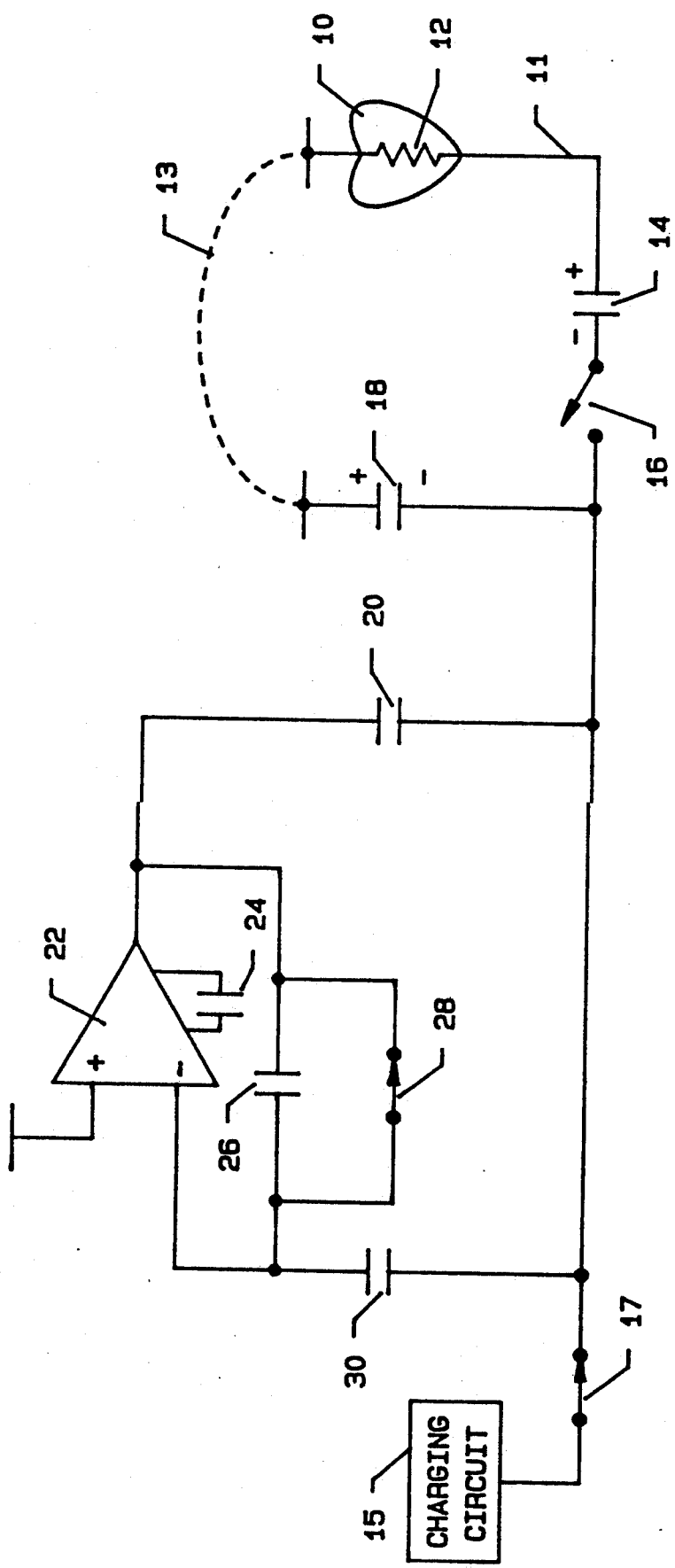
FIG. 1 is a schematic diagram of the pacer output circuit during charging of the output capacitor.

FIG. 1 is a schematic diagram of the major components of the cardiac pacer output circuit. Heart 10 of the patient presents resistive load 12 having a magnitude determined by various physiological factors. Resistive load 12 also contains the resistance of lead 11. Lead 11 is shown only as an electrical conductor in this schematic diagram. It has a resistance which is small in relation to the resistance within the body. Capacitor 14 is the series blocking capacitor to prevent DC current flow in the load. This is customarily used to prevent corrosion.

Single pole, single throw switch 16 is representative of the device which enables transfer of a pacing pulse through lead 11 to heart 10. A manual switch is shown for convenience, however, in practice the switch ordinarily consists of a semiconductor circuit.

Output capacitor 18 is charged between pacing pulses by charging circuit 15 which selects the output pacing voltage amplitude, and is discharged to provide the energy for the pacing pulse. This technique is helpful in meeting battery and size constraints for implantable devices because of the low duty cycle of the actual pacing output. Oftentimes external devices without these stringent battery and size constraints use similar circuit designs. Charging of output capacitor 18 occurs whenever single pole, single throw switch 17 is closed as shown. Output capacitor 18 discharges through heart 110 via lead 11 upon closing of single pole, single throw switch 16. Return path 13 is through the patient's body to the metal case of the implantable pulse generator for unipolar systems.

As output capacitor 18 is charged, it is connected to amplifier 22 via capacitors 20 and 30. Capacitor 24 controls the response of controlled gain amplifier 22, ensuring its stability. The input and output of amplifier 22 are connected together through switch 28 during this mode. The effect of this connection is to cause the amplifier offset voltage to be present at its output and input terminals. The value of voltage across capacitors 20 and 30 is thus the difference of the voltage on capacitor 18 and the amplifier's offset voltage.

Figure 2:
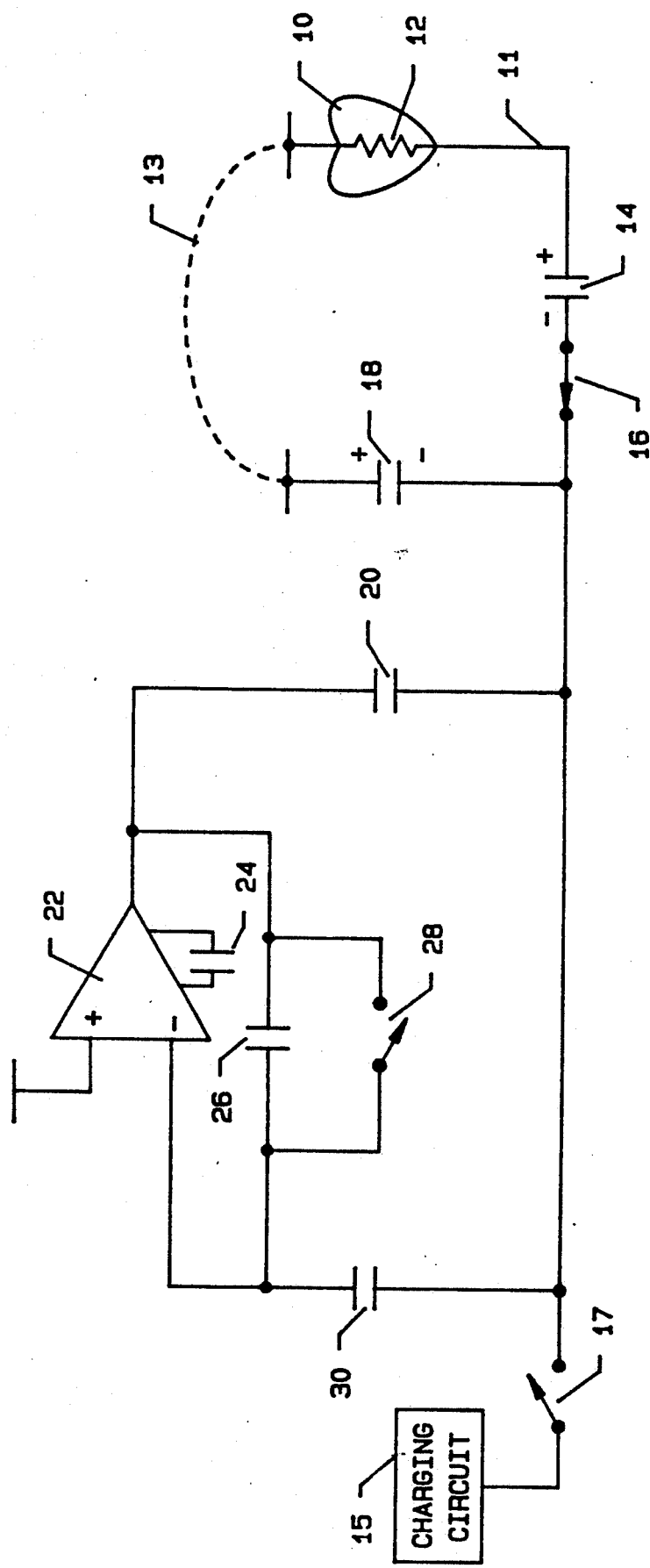
FIG. 2 is a schematic diagram of the output circuit during a pacing pulse which causes a discharging of the output capacitor.

FIG. 2 is a schematic of the circuit of FIG. 1 shown during transfer of the pacing pulse to heart 10. Pacing occurs when single pole, single throw switch 16 is closed permitting output capacitor 18 to discharge through capacitor 14 and resistive load 12 of heart 10. The return path 13 is via the body for unipolar applications. Single pole, single throw switch 28 is shown in the open state. The remaining referenced elements are as previously described.

During this stage, the voltage loss on capacitor 18 is inverted (and possibly scaled) by the amplifier and capacitors 30 and 26. The resultant output is impressed on capacitor 20. At the end of the pacing output period, capacitor 20 has a voltage stored on it equal to the original voltage decreased by the sum of the output voltage drop, the scaled output voltage drop, and the amplifier offset voltage.

Figure 3:
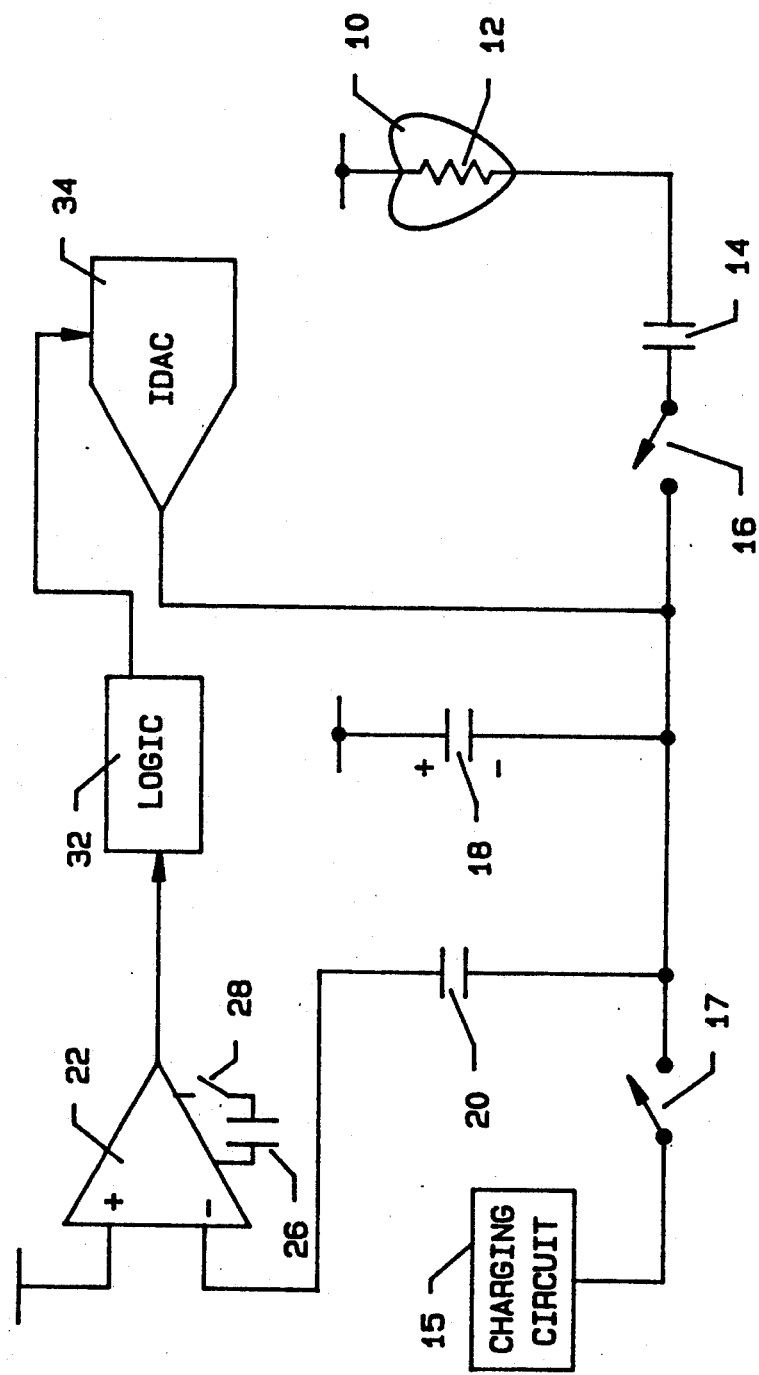
FIG. 3 is a schematic diagram showing how charge loss is determined.

FIG. 3 is a schematic diagram of the output circuit of FIG. 1 showing connection of the elements which provide the timing to control the measurement of lead current. During this phase, single pole, single throw switch 16 is open.

The digital to analog converter, IDAC 34, provides a current output which may be digitally programmed using standard techniques. A fixed current source may likewise be employed. This current is set to a convenient value by the control logic. Capacitor 20 is then connected to the input of the amplifier. The amplifier is then operated as a comparator and may be modified for higher speed by opening switch 28 to remove compensation capacitor 26 from the circuit. Because of the voltage stored in capacitor 20, the comparator will change state when capacitor 18 has been further discharged by an amount proportional (through the scaling of the previous step) to the drop due to the output pulse.

Logic 32 measures the length of time required to discharge output capacitor 18 according to the voltage as impressed on capacitor 20. Similarly logic 32 measures the length of time during which output capacitor 18 discharges. Because the capacitance of output capacitor 18 is fixed, the current through the discharge circuit (i.e. termed lead current) can be determined by controlling the gain of amplifier 22 as explained above and by knowing the IDAC current and discharge time of output capacitor 18. The remaining referenced elements are as previously described.

Figure 4:
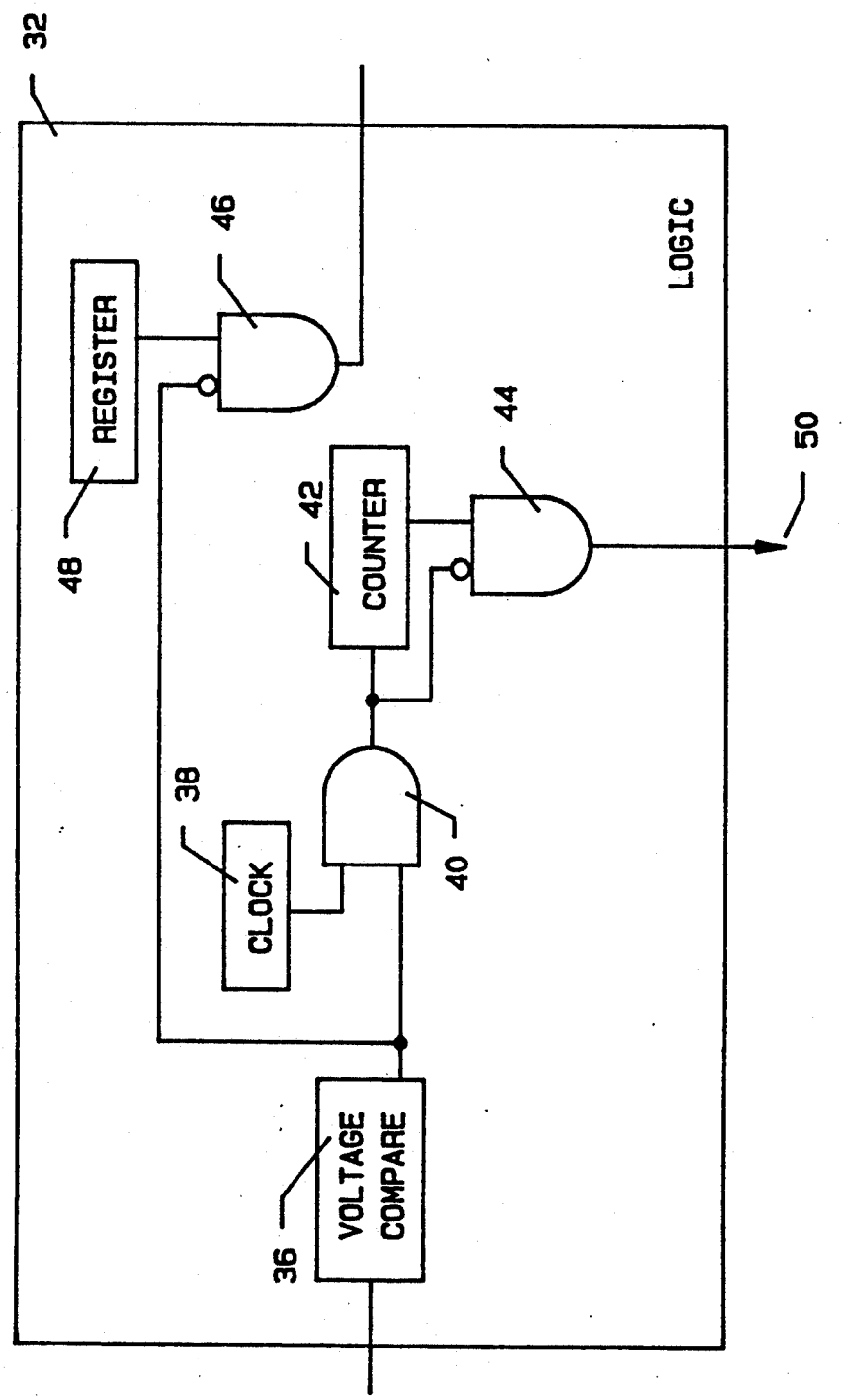
FIG. 4 is a schematic diagram of the control logic.

FIG. 4 is a block diagram of the operation of logic 32. Voltage compare 36 compares the voltage drop across output capacitor 18 to the programmed control voltage output during the discharging process. Until the voltages are equal, gate 40 enables the output of clock 38 to count up in counter 42. As soon as the voltages are equal, voltage compare 36 causes gate 40 to disable pulses from clock 38 for counter 42, thus freezing the count.

Similarly, when the voltages are equal, gate 44 enables an output of counter 42 as a representation of the length of time required to recharge output capacitor 18. Counter 42 must also be cleared using circuitry not shown before the counting is reinitiated.

Register 48 is preloaded with control current output at the time of programming the implantable pulse generator. Until the voltage comparison indicates completion of the discharge, the content of register 48 is enabled by gate 46 to IDAC 34 (see also FIG. 3), setting the value of the discharge current.

Figure 5:
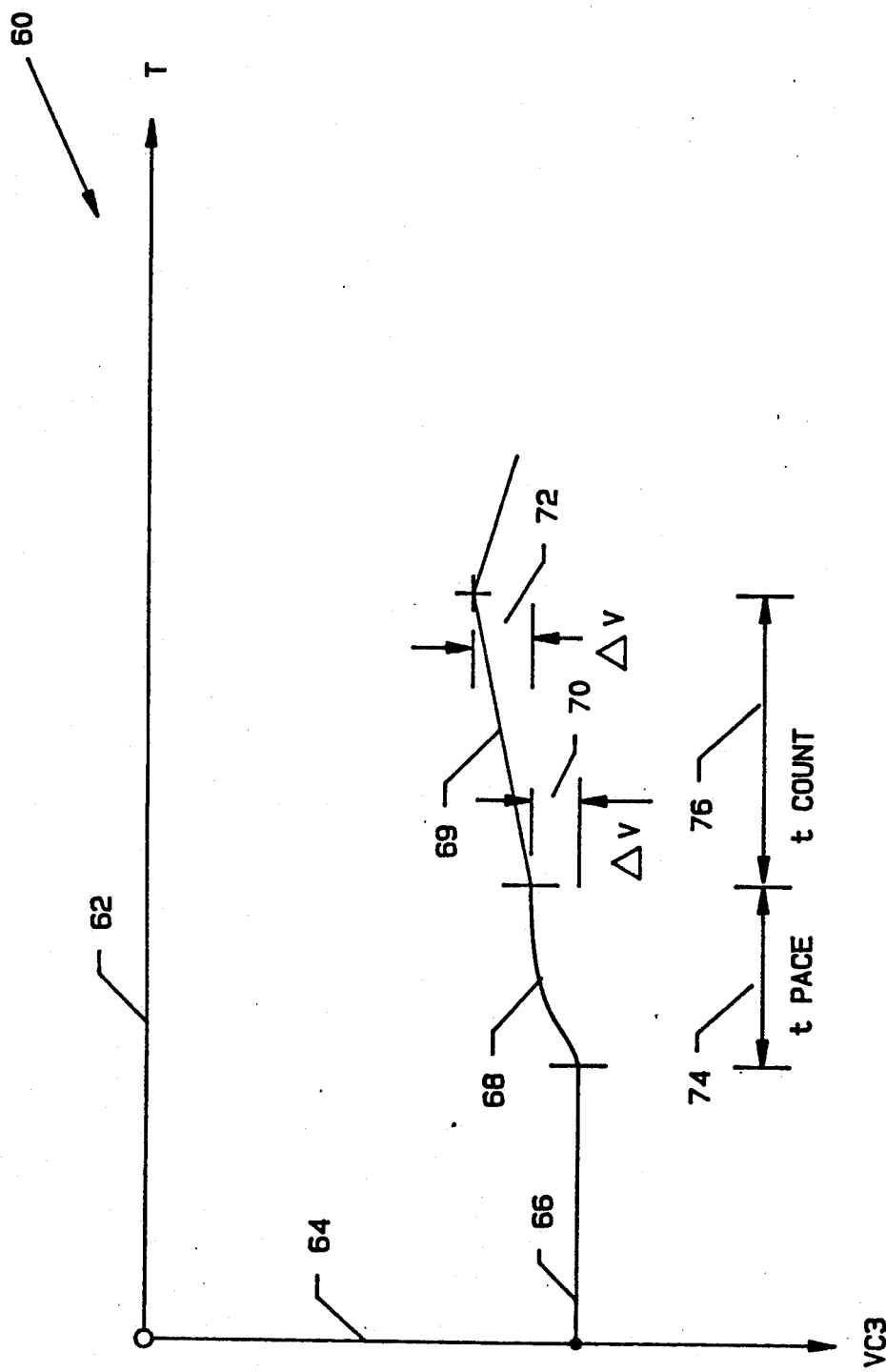
FIG. 5 is a graphical representation of the voltage drop across the output capacitor.

FIG. 5 is a graphical representation 60 of the voltage 64 of output capacitor 18 over time 62. Note the voltage is measured as a negative quantity. Voltage 66 represents the quiescent fully charged state. Curve 68 shows the discharge as a result of the delivery of a pacing pulse. Curve 69 shows the discharge activity. Note that the baseline shifts during this interval because output capacitor 18 is discharged using the IDAC.

The pace output time 74 is relatively short compared to discharge time (i.e. count 76). However, the change of voltage 70, as a result of pace output discharging, is equal with (or perhaps scaled proportionally to) the change of voltage 72 as a result of IDAC discharging. The resulting lead current becomes the reference current from the IDAC times the ratio of the IDAC discharge time (i.e. count 76) to the pace discharge time (i.e. pace 74).

Having thus described the preferred embodiments of the present invention, those of skill in the art will readily appreciate that various other embodiments of the present invention may be made and used from the teachings found herein within the scope of the claims hereto attached.

10 heart
11 lead
12 resistive load
13 return path
14 capacitor
15 circuit
16 single pole, single throw switch
17 switch
18 output capacitor
20 capacitor
22 controlled gain amplifier
24 capacitor
26 capacitor
28 single pole, single throw switch
30 capacitor
32 logic
34 digital to analog converter IDAC
36 voltage compare
38 clock
40 gate
42 counter
44 gate
46 gate
48 register
60 graphical representation
62 time
64 voltage
66 voltage
68 curve
69 curve
70 voltage
72 voltage
74 pace output time
76 count

We claim:
1. A method of measuring the current within the output circuit of an artificial pacing system comprising:
   a. charging an output capacitor using a reference circuit to a predetermined voltage;
   b. discharging said output capacitor producing an artificial pacing pulse;

c. determining the length of time of said artificial pacing pulse;

d. further discharging said output capacitor to produce a reference current;

e. measuring the time of said further discharging said output capacitor; and, f. computing said current within said output circuit of said artificial pacing system as said reference current of said further discharging multiplied by said length of time required to perform step b divided by said time of said further discharging.

2. A method according to claim wherein said predetermined voltage is a programmable parameter.

3. A method according to claim 2 wherein said time of said discharge step is a pacing pulse width.

4. An apparatus for measuring the output current of a cardiac pacer comprising:

a. an output capacitor;

b. a system for charging said output capacitor;

c. means for discharging said output capacitor for producing an artificial pacing pulse;

d. means coupled to said output capacitor and said system for determining when said output capacitor has been discharged to a predetermined voltage;

e. means for measuring the time for said system to discharge said output capacitor to said predetermined voltage and, f. means coupled to said determining means and said measuring means for calculating said output current.

5. An apparatus according to claim 4 wherein said determining means further comprises means for programming said predetermined voltage.

6. An apparatus according to claim 5 further comprising means for computing current of said output capacitor during discharge.

7. An apparatus according to claim 6 wherein said computing means further comprises means for finding said output current as the charging current multiplied by said charging time divided by said discharging time.

8. In a cardiac pacing system, having a circuit for charging an output capacitor at a reference current and means for discharging said output capacitor through a pacing lead, the improvement for measuring current through said pacing lead comprising:

a. means for measuring the time for said circuit to charge said output capacitor; and, b. means coupled to said measuring means for calculating said current through said pacing lead as a function of said measured time for said circuit to charge said output capacitor.

9. The improvement of claim 8 further comprising means for comparing a control voltage to the voltage of said output capacitor to determine an end to said time for said circuit to charge said output capacitor.

* * * * *

UNITED STATES PATENT AND TRADEMARK OFFICE
CERTIFICATE OF CORRECTION

PATENT NO. : 5,137,021

DATED : August 11, 1992

INVENTOR(S) : David A. Wayne, and Tho Huynh

It is certified that error appears in the above-indentified patent and that said Letters Patent is hereby corrected as shown below:

Column 2, Line 59, delete "110", and insert in its place --10--.

Column 5, Line 12, after "claim", add --1--.

Signed and Sealed this

Thirteenth Day of September, 1994

Attest:

BRUCE LEHMAN

Attesting Officer     Commissioner of Patents and Trademarks